United States Patent [19]

Saito et al.

[11] Patent Number: 5,136,104
[45] Date of Patent: Aug. 4, 1992

[54] METHOD FOR PRODUCTION OF SUBSTITUTED BENZALDEHYDE

[75] Inventors: Noboru Saito, Takatsuki; Isao Nakamura, HigashiOsaka; Michio Ueshima, Takarazuka; Kazuhiro Takatsu, Kashihara; Isao Nagai, Suita, all of Japan

[73] Assignee: Nippon Shokubai Kagaku Kogyo Co. Ltd., Osaka, Japan

[21] Appl. No.: 26,760

[22] PCT Filed: Nov. 11, 1985

[86] PCT No.: PCT/JP85/00628
§ 371 Date: Nov. 11, 1985
§ 102(e) Date: Nov. 11, 1985

[87] PCT Pub No. WO86/06715
PCT Pub Date. Nov. 20, 1986

[30] Foreign Application Priority Data

May 14, 1985 [JP] Japan .................. 60-100582

[51] Int. Cl.$^5$ .................. C07C 45/36; C07C 51/255
[52] U.S. Cl. .................. 568/431; 568/432; 562/415
[58] Field of Search .................. 568/431, 432; 562/415

[56] References Cited

U.S. PATENT DOCUMENTS 4,054,607 10/1977 Matsuoka .................. 260/600 R
4,137,259 1/1979 Van Geem et al. .................. 562/415

FOREIGN PATENT DOCUMENTS 1147997 4/1969 United Kingdom .

Primary Examiner—Jose G. Dees
Assistant Examiner—Porfirio Nazario
Attorney, Agent, or Firm—Omri M. Behr

[57] ABSTRACT

From a methoxy-, tertiary butyl-, or phenoxy-substituted toluene, a corresponding substituted benzaldehyde is obtained by the catalytic gas-phase oxidation of the substituted toluene with a molecular oxygen-containing gas in the presence of a catalyst composition represented by the formula, $V_a X_b Y_c O_d$, wherein X stands for at least one element from among Na, K, Rb, Cs, and Tl (with the exception of a case wherein K is used alone), Y for at least one element from among Mg, Ca, Sr, Ba, Nb, Ta, P, Sb, Bi, Cu, Ag, Ti, Fe, Co, Ni, Sn, Ce, and Zn, and a, b, c, and d jointly represent an atomic ratio of the relevant elements.

6 Claims, No Drawings

METHOD FOR PRODUCTION OF SUBSTITUTED BENZALDEHYDE

DESCRIPTION

1. Technical Field

This invention relates to a method for the production of a substituted benzaldehyde. More particularly, this invention relates to a method for the production in a high yield of a substituted benzaldehyde by the catalytic gas-phase oxidation of a substituted toluene. Yet more particularly, this invention relates to a method for the production in a high yield of a substituted benzaldehyde represented by the general formula II:

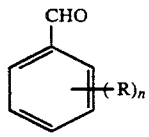
(II)

wherein R stands for methoxy group, tertiary butyl group, or phenoxy group and n for an integer of the value of 1 to 3, by the catalytic gas-phase oxidation of a substituted toluene represented by the general formula I:

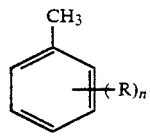
(I)

wherein R and n have the same meanings as defined above, with a molecular oxygen-containing gas.

2. Background Art

Heretofore, as means of synthesizing benzaldehydes by the partial oxidation of toluenes, the methods resorting to liquid-phase oxidation or electrolytic oxidation have been known to the art (as disclosed in the specification of Japanese Patent Publication SHO 55(1980)-42,974, Japanese Patent Laid-open SHO 54(1979)-109,937, Japanese Patent Laid-open SHO 55(1980)-85,682, and Japanese Patent Laid-open SHO 56(1981)-127,327). Then, as means of producing tertiary butyl or pheoxy-substituted benzaldehyde, the methods resorting to liquid-phase oxidation, electrolytic oxidation, or halogenation-hydrolysis of a compound represented by the aforementioned general formula (I) with a reagent have been known (as disclosed in the specification of Japanese Patent Laid-open SHO 52(1977)-125,137; Journal of Synthetic Organic Chemistry, Japan. Vol. 37, No. 8, p 667; and Journal of The National Chemical Laboratory for Industry Vol. 78, No. 2, p 19). When these methods are to be put to work commercially, however, they entail various problems such as inevitable requirement for a step of waste water disposal, excessively heavy consumption of electricity, and excessive complication of procedure. Thus, they cannot be called economically advantageous.

For the solution of these problems, therefore, a method of production resorting to commercially advantageous gas-phase oxidation is expected. Besides the methods mentioned above, methods for producing benzaldehydes by catalytic gas-phase oxidation of such methylbenzens as toluene, xylene, pseudocumene, and durene have been known to the art (as disclosed in West German Patent No. 1,947,994, U.S. Pat. No. 4,137,259, and Japanese Patent Publication SHO 51(1976)-33,101). These methods carry out their respective reactions by using vanadium type and tungsten-molybdenum type catalysts. The yields of these reactions are invariably low.

As regards the gas-phase oxidation of methoxy-substituted toluene, for example, a molybdenum-bismuth-iron-nickel type catalyst is disclosed (in the specification of West German Patent No. 2,841,712). This catalyst has no economic value because the yield of the oxidation is extremely low.

In the specification of Japanese Patent Publication SHO 58(1983)-4,012, a catalyst composed of vanadium, phosphorus, potassium sulfate, and copper is proposed for the production of anisaldehyde (p-methoxy benzaldehyde) by the oxidation of p-methoxy toluene and this catalyst is reported to have produced anisaldehyde in an one-pass yield of 65.0 mol %. In this case, however, the conversion of p-methoxy toluene is as low as 71.5 mol %, although the reaction temperature is as high as 495° C. Since this catalyst contains a large proportion of potassium sulfate which is held to be thermally unstable, it has room for doubt about catalyst life. In view of the high price of p-methoxy toluene as the starting material, the fact that the conversion thereof is low renders the oxidation disadvantageous as a commercial means of production.

The methoxy-substituted benzaldehyde is expected to be a product of high purity especially when it is meant as a raw material for medicines and pesticides. When the catalysts disclosed in the aforementioned publications are used in the production of this raw material, they give rise to secondary products formed mainly of tarry substances. It has been demonstrated that the product of high purity cannot be obtained easily by the ordinary technique of separation and purification.

As regards the catalytic gas-phase oxidation of p-tertiary butyl toluene, for example, a molybdenum-bismuth-iron-nickel type catalyst (West German Patent No. 2,841,712) and a molybdenum-copper-tin type catalyst (Japanese Patent Laid-open SHO 58(1983)-189,131) have been known to the art. Concerning the catalytic gas-phase oxidation of m-phenoxy toluene, for example, a method using a molybdenum-bismuth-iron-phosphorus-magnesium type catalyst (British Patent No. 1,579,702) has been reported. The catalysts disclosed in these publications, however, are invariably extremely deficient in catalytic activity and selectivity.

An object of this invention, therefore, is to provide a novel method for the production of a substituted benzaldehyde.

Another object of this invention is to provide a method for the production in a high yield of a substituted benzaldehyde by the catalytic gas-phase oxidation of a substituted toluene.

DISCLOSURE OF INVENTION

These objects are accomplished by a method for the production of a substituted benzaldehyde represented by the general formula II:

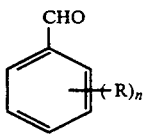

(II)

wherein R stands for methoxy group, tertiary butyl group, or phenoxy group and n for an integer of the value of 1 to 3, by the catalytic gas-phase oxidation of a substituted toluene represented by the general formula I:

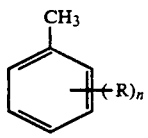

(I)

wherein R and n have the same meanings as defined above, with a molecular oxygen-containing gas in the presence of a catalyst composition represented by the general formula III:

$$V_a X_b Y_c O_d \quad (III)$$

wherein V stands for vanadium, O for oxygen, X for at least one element selected from the group consisting of sodium, potassium, rubidium, cesium, and thallium (with the exception of the case wherein potassium is used alone), Y for at least one element selected from the group consisting of magnesium, calcium, strontium, barium, niobium, tantalum, phosphorus, antimony, bismuth, copper, silver, titanium, iron, cobalt, nickel, tin, cerium, and zinc, and the subscripts a, b, c, and d represent such an atomic ratio of the relevant elements that where a=1 is assumed, b has a value in the range of 0.1 to 5, c has a value in the range of 0 to 5, and d has a value determined by the valencies of the other elements and the value of said atomic ratio.

BEST MODE OF CARRYING OUT THE INVENTION

In the substituted toluene of the general formula I to be used as the starting material in the method of this invention, n stands for an integer of the value of 1 to 3, more desirably for an integer of the value of 1 or 2, and most desirably for an integer of the value of 1. Typical substituted toluenes are o-methoxy toluene, p-methoxy toluene, m-methoxy toluene, 2,3-dimethoxy toluene, 2,4-dimethoxy toluene, 3,4-dimethoxy toluene, 2,5-dimethoxy toluene, 2,6-dimethoxy toluene, 2,3,4-trimethoxy toluene, 3,4,5-trimethoxy toluene, 2,4,6-trimethoxy toluene, o-tertiary butyl toluene, p-tertiary butyl toluene, m-tertiary butyl toluene, 2,4-ditertiary butyl toluene, p-phenoxy toluene, and m-phenoxy toluene.

Typical examples of the substituted benzaldehyde of the general formula II as the product include o-methoxy benzaldehyde, p-methoxy benzaldehyde (anisaldehyde), m-methoxy benzaldehyde, 2,3-dimethoxy benzaldehyde, 2,4-dimethoxy benzaldehyde, 3,4-dimethoxy benzaldehyde, 2,5-dimethoxy benzaldehyde, 2,6-dimethoxy benzaldehyde, 2,3,4-trimethoxy benzaldehyde, 3,4,5-trimethoxy benzaldehyde, 2,4,6-trimethoxy benzaldehyde, o-tertiary butyl benzaldehyde, p-tertiary butyl benzaldehyde, m-tertiary butyl benzaldehyde, 2,4-ditertiary butyl benzaldehyde, p-phenoxy benzaldehyde, and m-phenoxy benzaldehyde. Among other substituted benzaldehydes enumerated above, the products which can be produced in particularly high yields are p-methoxy benzaldehyde, 3,4-dimethoxy benzaldehyde, 3,4,5-trimethoxy benzaldehyde, p-tertiary butyl benzaldehyde, 2,4-ditertiary butyl benzaldehyde, p-phenoxy benzaldehyde, and m-phenoxy benzaldehyde.

The catalyst composition is represented by the general formula III:

$$V_a X_b Y_c O_d \quad (III)$$

wherein V and O respectively stand for vanadium and oxygen, X stands for at least one element selected from the group consisting of sodium, potassium, rubidium, cesium, and thallium (with the exception of the case wherein potassium is used alone), Y stands for at least one element selected from the group consisting of magnesium, calcium, strontium, barium, niobium, tantalum, phosphorus, antimony, bismuth, copper, silver, titanium, iron, cobalt, nickel, tin, cerium, and zinc, and the subscripts a, b, c, and d jointly represent such an atomic ratio of the relevant elements that when a=1 is assumed, b has a value in the range of 0.1 to 5, preferably 0.2 to 1.0, c has a value in the range of 0 to 5, preferably 0.1 to 1.0, and d has a value to be determined by the valencies of the other elements and the atomic ratio. Where R is methoxy group, however, (A) a combination wherein X is rubidium and/or cesium and Y is at least one element selected from the group consisting of copper, silver, phosphorus, antimony, and bismuth, particularly $V_1$-(Rb and/or Cs)$_{0.2-1.0}$-(Cu, Ag, P, Sb, or Bi)$_{0-1.0}$-$O_d$, (B) a combination wherien X is rubidium and/or cesium and potassium and Y is at least one element selected from the group consisting of copper, silver, phosphorus, antimony, and bismuth, particularly $V_1$-(Rb and/or Cs)-$_{0.01-1.0}$-$K_{0.01-1.0}$-(Cu, Ag, P, Sb, or Bi)$_{0-1.0}$-$O_d$, or (C) a 0.01-1.0 0.01-1.0-(Cu combination wherein X is thallium and at least one alkali metal selected from the group consisting of potassium, rubidium, and cesium and Y is at least one element selected from the group consisting of copper, silver, phosphorus, antimony, and bismuth, particularly $V_1$-$Tl_{0.01-1.0}$-(K, Rb, or Cs)$_{0-1.0}$-(Cu, Ag, P, Sb, or Bi)$_{0-1.0}$-$O_d$, proves particularly desirable.

In the production of the catalyst composition (A), use of a sulfate is desirable because no potassium is present. The salt so used remains as a sulfate radical in the catalyst and, in the method of the present invention, is effective in further enhancing the one-pass yield of the methoxy-substituted benzaldehyde. Since this catalyst is highly active, it manifests its effect for a long time and permits the reaction to proceed stably at a low reaction temperature without any possibility of the residual sulfate radical being scattered.

The catalyst composition (B) has no use particularly for the sulfate radical. Even when it contains the sulfate radical, the reaction temperature is so low that the catalytic activity is not observed to be degraded by the decomposition, scattering, etc. of the sulfate radical.

As concerns the starting materials for the catalyst composition to be specified in the present invention, ammonium metavanadate, vanadium pentoxide, vanadyl oxalate, vanadyl sulfate, etc. can be advantageously used as vanadium sources and nitrates, carbonates, sulfates, etc. as X element sources. Nitrates, oxalates, carbonates, acetates, sulfates, oxides, etc. can be advantageously used as Y element sources other than phosphorus. Phosphoric acid, ammonium phosphate, etc. can be advantageously used as phosphorus sources.

Although the catalyst can be molded solely of the essential components thereof, it is desired to be molded as admixed with an inactive powdered carrier such as silica, alumina, silicon carbide, zirconia, or titania. Otherwise, the carrier may be used as deposited on an inactive molded carrier such as spherical, cylindrical, ring-shaped, or fragments type carrier of silica, alumina, or silicon carbide.

The method generally used for the preparation of the catalyst of the present invention comprises first adding a compound as the X component element source to an aqueous solution containing a compound as the vanadium source, then adding a compound as the Y component element source thereto, further adding thereto a powdered carrier in an amount of 10 to 80% by weight based on the completed catalyst, evaporating the resultant mixture to dryness, subsequently drying the evaporation residue at 100° to 250° C., and thereafter calcining the dried residue at 450° to 750° C.

The catalytic gas-phase oxidation of a substituted toluene by the use of the catalyst prepared as described above can be advantageously carried out by feeding the raw material as contained at a concentration of 0.1 to 2% by volume in 98.0 to 99.9% by volume of air at a space velocity of 100 to 5,000 $hr^{-1}$ (STP standard), preferably 500 to 3,000 $hr^{-1}$, at a reaction temperature in the range of 300° to 500° C., preferably 330° C. to 480° C. Optionally, part of the air may be diluted with an inert gas such as steam, nitrogen, or carbon dioxide gas.

Now, the present invention will be described more specifically below with reference to working examples.

The conversion, the one-pass yield, and the selectivity as indicated in the working examples and the controls are in accordance with the definitions given below.

Conversion of substituted toluene (mol %) =

$$\frac{\text{Number of mols of reacted substituted toluene}}{\text{Number of mols of fed substituted toluene}} \times 100$$

One-pass yield of substituted benzaldehyde (mol %) =

$$\frac{\text{Number of mols of formed substituted benzaldehyde}}{\text{Number of mols of fed substituted toluene}} \times 100$$

Selectivity for substituted benzaldehyde (mol %) =

$$\frac{\text{Number of mols of formed substituted benzaldehyde}}{\text{Number of mols of reacted substituted toluene}} \times 100$$

EXAMPLE 1

To about 200 ml of warmed water, 10.7 g of ammonium metavanadate was added and then a solution of 7.16 g of cesium nitrate in about 50 ml of water was added. The resultant mixture was stirred at 70° C. for about one hour, admixed with 6.24 g of Celite (trademark designation), and concentrated by evaporation. The resultant concentrate was dried at 120° C. for 2 hours and then at 220° C. for 16 hours and calcined at 600° C. for 6 hours. The calcined mixture was pulverized into particles of 9 to 20 meshes. A 15-ml portion of the particles was placed in a stainless steel pipe 10 mm in inside diameter. This reaction tube was immersed in molten salts bath. The raw material gas was composed of 1.0% by volume of p-methoxy toluene and 99.0% by volume of air and subjected to reaction at space velocity of 3,000 $hr^{-1}$ (STP standard) at a reaction temperature of 400° C. The product was collected with acetone cooled to 0° C. with a scrubbing bottle. The uncollected $CO_2$ and CO were analyzed by TCD gas chromatography. The unaltered p-methoxy toluene and the produced anisaldehyde which were collected in the acetone were analyzed by FID gas chromatography. The results of the reaction are shown in Table 1.

EXAMPLE 2

The same procedure of Example 1 was carried out, except that 8.10 g of rubidium nitrate was used in place of cesium nitrate. The results are shown in Table 1.

CONTROL 1

The same procedure of Example 1 was carried out, except that 3.71 g of potassium nitrate was used in place of cesium nitrate. The results are shown in Table 1.

EXAMPLES 3–7

The same procedures of Example 1 were carried out, except that 4.45 g of copper nitrate, 3.13 g of silver nitrate, 2.13 g of 85% phosphoric acid, 2.68 g of antimony trioxide, and 8.94 g of bismuth nitrate were respectively added after the addition of cesium nitrate. The results are shown in Table 1.

EXAMPLE 8

The same procedure of Example 4 was carried out, except that 2.68 g of antimony trioxide was further added after the addition of silver nitrate. The results are shown in Table 1.

EXAMPLE 9

The same procedure of Example 3 was carried out, except that 2.13 g of 85% phosphoric acid was further added after the addition of copper nitrate. The results are shown in Table 1.

EXAMPLE 10

The same procedure of Example 1 was carried out, except that 10.0 g of cesium sulfate was used in place of cesium nitrate and 3.13 g of silver nitrate and 2.13 g of 85% phosphoric acid were further added thereafter. The results are shown in Table 1.

CONTROL 2

The same procedure of Example 10 was carried out, except that 12.1 g of potassium sulfate was used in place of cesium sulfate and the reaction temperature was changed to 500° C. The results are shown in Table 1.

While the reaction product in Example 10 was nearly colorless and transparent, that of this experiment was tinted in yellow. A high-boiling carbide was seen adhering to the output part of the reaction tube.

EXAMPLE 11

The same procedure of Example 10 was carried out, except that 3,4-dimethoxy toluene was used as the raw material and the catalyst in Example 10 was used. The results are shown in Table 1.

EXAMPLE 12

The same procedure of Example 10 was carried out, except that 3,4,5-trimethoxy toluene was used as the raw material and the catalyst obtained in Example 10 was used. The results are shown in Table 1.

TABLE 1

| | Composition of Catalyst | | | Conversion (mol %) | One-pass yield (mol %) Aldehyde | Selectivity (mol %) Aldehyde |
|---|---|---|---|---|---|---|
| | V | Rb and/or Cs | Cu, Ag, P, Sb, Bi | | | |
| Example 1 | 1.0 | Cs 0.4 | — | 95.1 | 68.9 | 72.5 |
| Example 2 | " | Rb 0.6 | — | 94.7 | 68.4 | 72.2 |
| Control 1 | " | K 1.0 | — | 80.5 | 28.1 | 34.9 |
| Example 3 | " | Cs 0.4 | Cu 0.2 | 92.1 | 73.6 | 79.9 |
| Example 4 | " | Cs 0.4 | Ag 0.2 | 98.8 | 73.4 | 74.3 |
| Example 5 | " | Cs 0.4 | P 0.2 | 99.1 | 74.7 | 75.4 |
| Example 6 | " | Cs 0.4 | Sb 0.2 | 93.2 | 72.1 | 77.4 |
| Example 7 | " | Cs 0.4 | Bi 0.2 | 93.5 | 71.9 | 76.9 |
| Example 8 | " | Cs 0.4 | Ag 0.2 Sb 0.2 | 95.1 | 77.9 | 81.9 |
| Example 9 | " | Cs 0.4 | Cu 0.2 P 0.2 | 95.5 | 78.6 | 82.3 |
| Example 10 | " | Cs 0.6 (Cs$_2$SO$_4$) | Ag 0.2 P 0.2 | 95.8 | 79.5 | 83.0 |
| Control 2 | " | K 1.5 (K$_2$SO$_4$) | P 0.2 | 80.1 | 48.7 | 60.8 |
| Example 11 | (The same catalyst as that used in Example 10) | | | 96.3 | 68.5 | 71.1 |
| Example 12 | (The same catalyst as that used in Example 10) | | | 97.4 | 66.4 | 68.2 |

EXAMPLE 13

To about 200 ml of warmed water, 10.7 g of ammonium metavanadate was added, then a solution of 3.57 g of cesium nitrate in about 50 ml of water was added, and subsequently a solution of 2.78 g of potassium nitrate in about 30 ml of water was added. The resultant solution was stirred at 70° C. for about 1 hour, admixed with 6.5 g of Celite (trademark designation), and concentrated by evaporation. The resultant concentrate was dried at 120° C. for 2 hours and then at 220° C. for 16 hours and calcined in the air at 600° C. for 6 hours.

The calcined mixture was pulverized into particles of 9 to 20 meshes and a 15-ml portion of the particles was placed in a stainless steel U tube 10 mm in inside diameter. A raw material gas consisting of 1.0% by volume of methoxy toluene and 99.0% by volume of air was fed at space velocity of 3,000 hr$^{-1}$ (STP standard) to the U tube and subjected to reaction therein at a reaction temperature of 370° C. The results of the reaction are shown in Table 2.

EXAMPLE 14

The same procedure of Example 13 was carried out, except that 4.05 g of rubidium nitrate was used in place of cesium nitrate and the amount of potassium nitrate was changed to 3.70 g. The results are shown in Table 2.

EXAMPLE 51

The same procedure of Example 13 was carried out, except that the catalyst was prepared by changing the amount of cesium nitrate used to 8.92 g and that of potassium nitrate to 0 and the reaction temperature was changed to 400° C. The results are shown in Table 2.

EXAMPLES 15-19

The same procedures of Example 13 were carried out, except that 2.21 g of copper nitrate, 1.55 g of silver nitrate, 3.16 g of 85% phosphoric acid, 4.00 g of antimony trioxide, and 13.32 g of bismuth nitrate were respectively added after the addition of cesium nitrate and potassium nitrate. The results are shown in Table 2.

EXAMPLE 20

The same procedure of Example 16 was carried out, except that 4.00 g of antimony trioxide was added after the addition of silver nitrate. The results are shown in Table 2.

EXAMPLE 21

The same procedure of Example 15 was carried out, except that 3.16 g of 85% phosphoric acid was further added after the addition of copper nitrate. The results are shown in Table 2.

EXAMPLE 22

The same procedure of Example 20 was carried out, except that cesium sulfate was used in place of cesium nitrate and the amount of this salt to be used was changed to 4.97 g. The results are shown in Table 2.

EXAMPLE 52

The same procedure of Example 21 was carried out, except that the catalyst was prepared by changing the amount of cesium nitrate to 8.92 g and the amount of potassium nitrate to 0 and the reaction temperature was changed to 400° C. The results are shown in Table 2.

EXAMPLES 23-24

The same procedures of Example 21 were carried out, except that 3,4-dimethoxy toluene and 3,4,5-trimethoxy toluene were respectively used as raw materials for the reactions. The results are shown in Table 2.

TABLE 2

| | Composition of Catalyst | | | | Reaction temperature (°C.) | Convertion (mol %) | One-pass yield of aldehyde (mol %) | Selectivity of aldehyde (mol %) |
|---|---|---|---|---|---|---|---|---|
| | V | K | Rb and/or Cs | Cu, Ag, P, Sb, Bi | | | | |
| Example 13 | 1 | 0.3 | Cs 0.2 | — | 370 | 93.7 | 72.1 | 76.9 |
| Example 14 | " | 0.4 | Rb 0.3 | — | 370 | 93.2 | 71.1 | 76.3 |

TABLE 2-continued

|  | Composition of Catalyst | | | | Reaction temperature (°C.) | Convertion (mol %) | One-pass yield of aldehyde (mol %) | Selectivity of aldehyde (mol %) |
| --- | --- | --- | --- | --- | --- | --- | --- | --- |
|  | V | K | Rb and/or Cs | Cu, Ag, P, Sb, Bi | | | | |
| Example 51 | " | 0 | Cs 0.5 | — | 400 | 92.5 | 67.4 | 72.9 |
| Example 15 | " | 0.3 | Cs 0.2 | Cu 0.1 | 370 | 91.4 | 74.2 | 81.4 |
| Example 16 | " | " | Cs 0.2 | Ag 0.1 | 370 | 97.9 | 74.8 | 76.4 |
| Example 17 | " | " | Cs 0.2 | P 0.3 | 370 | 98.6 | 76.1 | 77.2 |
| Example 18 | " | " | Cs 0.2 | Sb 0.3 | 370 | 92.2 | 73.4 | 79.6 |
| Example 19 | " | " | Cs 0.2 | Bi 0.3 | 370 | 92.4 | 73.1 | 79.1 |
| Example 20 | " | " | Cs 0.2 | Ag 0.1 Sb 0.3 | 370 | 94.8 | 80.7 | 85.1 |
| Example 21 | " | " | Cs 0.2 | Cu 0.1 P 0.3 | 370 | 95.2 | 81.9 | 86.0 |
| Example 22 | " | " | Cs 0.3 (Cs$_2$SO$_4$) | Ag 0.1 Sb 0.3 | 370 | 95.4 | 80.6 | 84.5 |
| Example 52 | " | 0 | Cs 0.5 | Cu 0.1 P 0.3 | 400 | 92.7 | 76.1 | 82.1 |
| Example 23 | | | (The same catalyst as that used in Example 21) | | 370 | 96.4 | 70.2 | 72.8 |
| Example 24 | | | (The same catalyst as that used in Example 21) | | 370 | 97.3 | 68.5 | 70.4 |

(Note) In all the experiments indicated above, the aldehyde aimed at was invariably anisaldehyde, except in Example 23 (3,4-dimethoxy benzaldehyde) and Example 24 (3,4,5-trimethoxy benzaldehyde).

EXAMPLE 25

To about 200 ml of warmed water, 10.7 g of ammonium metavanadate was added and a solution of 14.6 g of thallium nitrate in about 50 ml of water was added. The resultant solution was stirred at 70° C. for about 1 hour, admixed with 6.5 g of Celite (trademark designation), and concentrated by evaporation. The resultant concentrate was dried at 120° C. for 2 hours and then at 220° C. for 16 hours and calcined in the air at 600° C. for 6 hours.

The calcined mixture was pulverized into particles of 9 to 20 meshes and a 15-ml portion of the particles was placed in a stainless steel tube 10 mm in inside diameter. A raw material gas consisting of 1.0% by volume of p-methoxy toluene and 99.0% by volume of air was fed at a space velocity of 3,000 hr$^{-1}$ (STP standard) and subjected to reaction at a reaction temperature of 350° C. The results of the reaction are shown in Table 3.

EXAMPLES 26 and 27

The same procedures of Example 25 were carried out, except that thallium nitrate was added in respective amounts of 12.2 g and 9.7 g and, after the addition of the aqueous thallium nitrate solutions, solutions respectively of 1.85 g of potassium nitrate and 2.70 g of rubidium nitrate in about 30 ml of water were added. The results are shown in Table 3.

EXAMPLE 28

The same procedure of Example 26 was carried out, except that the amount of thallium nitrate was changed to 7.3 g and 3.57 g of cesium nitrate was used in place of potassium nitrate. A continuous reaction was carried out using this catalyst under the same reaction conditions. Even after about 10,000 hours' reaction, virtually no change was recognized in the yield. The results are shown in Table 3.

EXAMPLES 29-33

The same procedures of Example 25 were carried out, except that 2.21 g of copper nitrate, 1.55 g of silver nitrate, 3.16 g of 85% phosphoric acid, 4.00 g of antimony trioxide, and 13.32 g of bismuth nitrate were respectively added after the addition of the aqueous thallium nitrate solution. The results are shown in Table 3.

EXAMPLE 53

To about 200 ml of warmed water, 10.7 g of ammonium metavanadate was added and a solution of 8.91 g of cesium nitrate in about 50 ml of water was added. The resulting solution was stirred at 70° C. for about 1 hour, admixed with 6.5 g of Celite (trademark designation), and then subjected to a reaction by following the procedure of Example 25, except that the reaction temperature was changed to 400° C. The results are shown in Table 3.

CONTROL 6

The same procedure of Example 53 was carried out, except that 4.22 g of 85% phosphoric acid was used in place of cesium nitrate. The results are shown in Table 3.

EXAMPLES 34 and 35

The same procedures of Example 28 were carried out, except that 1.55 g of silver nitrate and 4.00 g of antimony trioxide were respectively added after the addition of cesium nitrate. The results are shown in Table 3.

EXAMPLE 36

The same procedure of Example 29 was carried out, except that 3.16 g of 85% phosphoric acid was further added after the addition of copper nitrate. When a continuous reaction was carried out using the resulting catalyst under the same conditions, virtually no change was recognized in the yield even after about 10,000 hours' reaction. The results are shown in Table 3.

EXAMPLE 37

The same procedure of Example 28 was carried out, except that 1.55 g of silver nitrate and 3.16 g of 85% phosphoric acid were further added after the addition of cesium nitrate. The results are shown in Table 3.

EXAMPLE 54

The same procedure of Example 37 was carried out, except that the amount of thallium nitrate used was changed to 0 and that of cesium nitrate to 8.91 g and the reaction temperature was changed to 400° C. The results are shown in Table 3.

TABLE 3

| Example | Composition of catalyst (Except for oxygen) V | Tl | K, Rb, Cs Cu, Ag, P, Sb, Bi | | | Reaction temperature (°C.) | Conversion of p-methoxy toluene (mol %) | One-pass yield of anisaldehyde (mol %) | Selectivity of anisaldehyde (mol %) |
|---|---|---|---|---|---|---|---|---|---|
| Example | | | | | | | | | |
| 25 | 1.0 | 0.6 | — | | | 350 | 93.4 | 71.5 | 76.6 |
| 26 | " | 0.5 | K 0.2 | | | " | 96.5 | 73.7 | 76.4 |
| 27 | " | 0.4 | Rb 0.2 | | | " | 93.1 | 73.4 | 78.8 |
| 28 | " | 0.3 | Cs 0.2 | | | " | 93.8 | 74.3 | 79.2 |
| | | | After 10,000 hours' continuous reaction | | | " | 92.7 | 73.6 | 79.4 |
| 29 | " | 0.6 | Cu 0.1 | | | " | 92.2 | 76.9 | 83.4 |
| 30 | " | " | Ag 0.1 | | | " | 96.2 | 77.2 | 80.2 |
| 31 | " | " | P 0.3 | | | " | 98.3 | 80.2 | 81.6 |
| 32 | " | " | Sb 0.3 | | | " | 92.4 | 76.3 | 82.6 |
| 33 | " | " | Bi 0.3 | | | " | 92.6 | 76.1 | 82.2 |
| Example 53 | " | 0 | Cs 0.5 | | | 400 | 92.5 | 67.4 | 72.9 |
| Control 6 | " | " | P 0.4 | | | " | 99.5 | 25.1 | 25.2 |
| Example | | | | | | | | | |
| 34 | " | 0.3 | Cs 0.2 | Ag 0.1 | | 350 | 96.4 | 82.6 | 85.7 |
| 35 | " | " | Cs 0.2 | Sb 0.3 | | " | 92.8 | 80.9 | 87.2 |
| 36 | " | 0.6 | Cu 0.1 | P 0.3 | | " | 95.3 | 80.4 | 84.4 |
| | | | After 10,000 hours' continuous reaction | | | " | 94.5 | 80.1 | 84.8 |
| 37 | " | 0.3 | Cs 0.2 | Ag 0.1 | P 0.3 | " | 94.6 | 83.7 | 88.5 |
| Example 54 | " | 0 | Cs 0.5 | Ag 0.1 | P 0.3 | 400 | 93.1 | 75.9 | 81.5 |

EXAMPLES 38 and 39

The same procedures of Example 37 were carried out, except that 3,4-dimethoxy toluene and 3,4,5-trimethoxy toluene were respectively used as raw materials for reaction. The results are shown in Table 4.

TABLE 4

| Example | Reaction temperature (°C.) | Conversion of raw material (mol %) |
|---|---|---|
| 38 | 350 | 95.9 |
| 39 | 350 | 96.7 |

| Example | One-pass yield of aldehyde (mol %) | Selectivity of aldehyde (mol %) |
|---|---|---|
| 38 | 72.1 | 75.2 |
| 39 | 70.3 | 72.7 |

The aldehyde products consequently obtained were 3,4-dimethoxy benzaldehyde in Example 38 and 3,4,5-trimethoxy benzaldehyde in Example 39.

EXAMPLE 40

To about 300 ml of warmed water, 11.7 g of ammonium metavanadate was added and a solution of about 5.85 g of cesium nitrate in about 50 ml of water was added. The resultant solution was stirred at 70° C. for about 1 hour, admixed with 6.82 g of Celite (trademark designation), and concentrated by evaporation. The concentrate was dried at 120° C. for 2 hours and then at 220° C. for 16 hours and calcined at 600° C. for 6 hours. Consequently, there was obtained an oxide of a catalyst composition, $V_1Cs_{0.3}$, in atomic ratio except for oxygen. The composite was pulverized into particles of 9 to 20 meshes and a 15-ml portion of the particles was placed in stainless steel U tube 10 mm in inside diameter. A raw material consisting of 1.0% by volume of p-tertiary butyl toluene and 99.0% by volume of air was fed at a space velocity of 3,000 hr$^{-1}$ (STP standard) and subjected to reaction at a reaction temperature of 450° C. The results are shown in Table 5.

EXAMPLE 41

The same procedure of Example 40 was carried out, except that a solution of 3.40 g of silver nitrate in about 10 ml of water was further added after the addition of cesium nitrate. Consequently, there was obtained an oxide of a catalyst composition, $V_1Cs_{0.3}Ag_{0.2}$, in atomic ratio except for oxygen. A reaction was carried out using the resultant catalyst by following the procedure of Example 40, except that the reaction temperature was changed to 420° C. The results are shown in Table 5.

EXAMPLE 42

The same procedure of Example 41 was carried out, except that 2.31 g of 85% phosphoric acid was added in place of silver nitrate. Consequently, there was obtained an oxide of a catalyst composition, $V_1Cs_{0.3}P_{0.2}$, in atomic ratio except for oxygen. A reaction was carried out using the resultant catalyst by following the procedure of Example 41. The results are shown in Table 5.

EXAMPLE 43

The same procedure of Example 40 was carried out, except that 5.90 g of rubidium nitrate was added in place of cesium nitrate and, after the addition of rubidium nitrate, a solution of 2.56 g of magnesium nitrate in about 10 ml of water and 0.80 g of titanium dioxide were added. Consequently, there was obtained an oxide of a catalyst composition, $V_1Rb_{0.4}Mg_{0.1}Ti_{0.1}$, in atomic ratio except for oxygen. A reaction was carried out using the resultant catalyst by following the procedure of Example 41. The results are shown in Table 5.

EXAMPLE 44

The same procedure of Example 41 was carried out, except that 5.43 g of cesium sulfate was added in place of cesium nitrate and a solution of 1.51 g of tin dioxide and 4.35 g of cerium nitrate in about 10 ml of water was added in place of silver nitrate. Consequently, there was obtained an oxide of a catalyst composition, $V_1Cs_{0.3}Sn_{0.1}Ce_{0.1}$, in atomic ratio except for oxygen. A reaction was carried out using the resultant catalyst by following the procedure of Example 41. The results are shown in Table 5.

EXAMPLE 45

The same procedure of Example 40 was carried out, except that 7.99 g of thallium nitrate was added in place of cesium nitrate and, after the addition of thallium nitrate, a solution of 2.36 g of calcium nitrate in about 10 ml of water and 1.46 g of antimony trioxide were added. Consequently, there was obtained an oxide of a catalyst composition, $V_1Tl_{0.3}Ca_{0.1}Sb_{0.1}$, in atomic ratio except for oxygen. A reaction was carried out using the resultant catalyst by following the procedure of Example 41. The results are shown in Table 5.

EXAMPLE 46

The same procedure of Example 40 was carried out, except that a solution of 0.85 g of sodium nitrate in about 10 ml of water and a solution of 2.31 g of 85% phosphoric acid, 2.61 g of barium nitrate, and 2.12 g of strontium nitrate in about 10 ml of water were added after the addition of cesium nitrate. Consequently, there was obtained an oxide of a catalyst composition, $V_1Cs_{0.3}Na_{0.1}P_{0.2}Ba_{0.1}Sr_{0.1}$, in atomic ratio except for oxygen. A reaction was carried out using the resultant catalyst by following the procedure of Example 41. The results are shown in Table 5.

EXAMPLE 47

The same procedure of Example 40 was carried out, except that a solution of 1.01 g of potassium nitrate in about 10 ml of water and a solution of 1.16 g of 85% phosphoric acid and 2.42 g of copper nitrate in about 10 ml of water were added after the addition of cesium nitrate. Consequently, there was obtained an oxide of a catalyst composition, $V_1Cs_{0.3}K_{0.1}P_{0.1}Cu_{0.1}$, in atomic ratio except for oxygen. A reaction was carried out using the resultant catalyst by following the procedure of Example 41. The results are shown in Table 5.

CONTROL 8

The same procedure of Example 47 was carried out, except that the addition of cesium and potassium nitrate was omitted. Consequently, there was obtained an oxide of a catalyst composition, $V_1P_{0.1}Cu_{0.1}$, except for oxygen. A reaction was carried out using the resultant catalyst by following the procedure of Example 41. The results are shown in Table 5.

TABLE 5

| | Composition of catalyst | | | Reaction temperature (°C.) | Conversion of p-tertiary butyl toluene (mol %) | One-pass yield p-tertiary butyl benzaldehyde (mol %) | Slectivity of p-tertiary butyl benzaldehyde (mol %) |
|---|---|---|---|---|---|---|---|
| | V | X component element | Y component element | | | | |
| Example | | | | | | | |
| 40 | 1 | Cs 0.3 | — | 450 | 71.8 | 41.4 | 57.7 |
| 41 | 1 | Cs 0.3 | Ag 0.2 | 420 | 70.4 | 45.1 | 64.1 |
| 42 | 1 | Cs 0.3 | P 0.2 | 420 | 70.1 | 46.1 | 65.8 |
| 43 | 1 | Rb 0.4 | Mg 0.1 Ti 0.1 | 420 | 79.3 | 50.7 | 63.9 |
| 44 | 1 | Cs 0.3 | Sn 0.1 Ce 0.1 | 420 | 82.1 | 53.4 | 65.0 |
| 45 | 1 | Tl 0.3 | Ca 0.1 Sb 0.1 | 420 | 79.3 | 54.2 | 68.3 |
| 46 | 1 | Cs 0.3 Na 0.1 | P 0.2 Ba 0.1 Sr 0.1 | 420 | 82.3 | 55.1 | 67.0 |
| 47 | 1 | Cs 0.3 K 0.1 | P 0.1 Cu 0.1 | 420 | 81.6 | 56.2 | 68.9 |
| Control 8 | 1 | — | P 0.1 Cu 0.1 | 420 | 84.5 | 5.6 | 6.6 |

EXAMPLE 48

The same procedure of Example 47 was carried out except that a solution of 4.04 g of iron nitrate in about 10 ml of water and a solution of 2.91 g of cobalt nitrate in about 10 ml of water were added in place of copper nitrate. Consequently, there was obtained an oxide of a catalyst composition, $V_1Cs_{0.3}K_{0.1}P_{0.1}Fe_{0.1}Co_{0.1}$, in atomic ratio except for oxygen. A reaction was carried out using the resultant catalyst by following the procedure of Example 40, except that the reaction temperature was changed to 360° C. The results are shown in Table 6.

CONTROL 9

The same procedure of Example 48 was carried out, except that the addition of cesium nitrate and potassium nitrate was omitted. Consequently, there was obtained an oxide of a catalyst composition, $V_1P_{0.1}Fe_{0.1}Co_{0.1}$, in atomic ratio except for oxygen. A reaction was carried out using the resultant catalyst by following the procedure of Example 48. The results are shown in Table 6.

TABLE 6

| | Composition of catalyst | | | Reaction temperature (°C.) | Conversion of p-phenoxy toluene (mol %) | One-pass yield of p-phenoxy benzaldehye (mol %) | Selectivity of p-phenoxy benzaldehyde (mol %) |
|---|---|---|---|---|---|---|---|
| | V | X component element | Y component element | | | | |
| Example 48 | 1 | Cs 0.3 K 0.1 | P 0.1 Fe 0.1 Co 0.1 | 360 | 93.2 | 75.3 | 80.8 |
| Control 9 | 1 | — | P 0.1 Fe 0.1 | 360 | 95.9 | 9.8 | 10.2 |

TABLE 6-continued

| | Composition of catalyst | | Reaction temperature (°C.) | Conversion of p-phenoxy toluene (mol %) | One-pass yield of p-phenoxy benzaldehye (mol %) | Selectivity of p-phenoxy benzaldehyde (mol %) |
| --- | --- | --- | --- | --- | --- | --- |
| V | X component element | Y component element | | | | |
| | Co 0.1 | | | | | |

EXAMPLE 49

The same procedure of Example 47 was carried out, except that 0.87 g of potassium sulfate was used in place of potassium nitrate, a solution of 4.85 g of bismuth nitrate in about 10 ml of nitric acid, a solution of 2.97 g of zinc nitrate in about 10 ml of water, and 1.33 g of niobium pentoxide were added in place of phosphoric acid and copper nitrate. Consequently, there was obtained an oxide of a catalyst composition, $V_1Cs_{0.3}K_{0.1}Bi_{0.1}Zn_{0.1}Nb_{0.1}$, using the resultant catalyst by following the procedure of Example 41, except that m-phenoxy toluene was used as a raw material for the reaction. The results are shown in Table 7.

CONTROL 10

The same procedure of Example 49 was carried out, except that the addition of cesium nitrate and potassium sulfate was omitted. Consequently, there was obtained an oxide of a catalyst composition, $V_1Bi_{0.1}Zn_{0.1}Nb_{0.1}$, in atomic ratio except for oxygen. A reaction was carried out using the resultant catalyst by following the procedure of Example 49. The results are shown in Table 7.

EXAMPLE 50

The same procedure of Example 40 was carried out, except that the amount of cesium nitrate added was changed to 3.90 g and, after the addition of cesium nitrate, a solution of 2.95 g of rubidium nitrate in about 10 ml of water, a solution of 1.46 g of antimony trioxide and 2.91 g of nickel nitrate in about 10 ml of water, and 2.21 g of tantalum pentoxide were added. Consequently, there was obtained an oxide of a catalyst composition, $V_1Cs_{0.2}Rb_{0.2}Sb_{0.1}Ni_{0.1}Ta_{0.1}$, in atomic ratio except for oxygen. A reaction was carried out using the resultant catalyst by following the procedure of Example 41, except that 2,4-ditertiary butyl toluene was used as a raw material for the reaction. The results are shown in Table 8.

CONTROL 11

The same procedure of Example 50 was carried out, except that the addition of cesium nitrate and rubidium nitrate was omitted. Consequently, there was obtained an oxide of a catalyst composition, $V_1Sb_{0.1}Ni_{0.1}Ta_{0.1}$, in atomic ratio except for oxygen. A reaction was carried out using the resultant catalyst by following the procedure of Example 50. The results are shown in Table 8.

TABLE 8

| | | Composition of catalyst | | Reaction temperature (°C.) | Conversion of 2,4-ditertiary butyl toluene (mol %) | One-pass yield of 2,4-ditertiary butyl benzaldehyde (mol %) | Selectivity of 2,4-ditertiary butyl benzaldehyde (mol %) |
| --- | --- | --- | --- | --- | --- | --- | --- |
| | V | X component element | Y component element | | | | |
| Example 50 | 1 | Cs 0.2 Rb 0.2 | Sb 0.1 Ni 0.1 Ta 0.1 | 420 | 92.1 | 55.1 | 59.8 |
| Control 11 | 1 | — | Sb 0.1 Ni 0.1 Ta 0.1 | 420 | 97.5 | 5.4 | 5.5 |

INDUSTRIAL APPLICABILITY

As described above, a substituted benzaldehyde is obtained in an extremely high yield from a corresponding substituted toluene accordance with the present invention. In the synthesis of an anisaldehyde by the catalytic gas-phase oxidation of a p-methoxy toluene, for example, an extremely high conversion of the p-methoxy toluene and an extremely high one-pass yield of the anisaldehyde are accomplished at a relatively low reaction temperature in the range of 350° to 400° C.

TABLE 7

| | | Composition of catalyst | | Reaction temperature (°C.) | Conversion of m-phenoxy toluene (mol %) | One-pass yield of m-phenoxy benzaldehye (mol %) | Selectivity of m-phenoxy benzaldehyde (mol %) |
| --- | --- | --- | --- | --- | --- | --- | --- |
| | V | X component element | Y component element | | | | |
| Example 49 | 1 | Cs 0.3 K 0.1 | Bi 0.1 Zn 0.1 Nb 0.1 | 420 | 75.1 | 39.6 | 52.7 |
| Control 10 | 1 | — | Bi 0.1 Zn 0.1 Nb 0.1 | 420 | 83.5 | 4.8 | 5.7 |

Even when the reaction is continued for a period of six months or one year, it can be retained stably. This reaction affords a product of very high purity and great ease of purification while entailing occurrence of virtually no secondary products except for carbon dioxide and carbon monoxide. The produced substituted benzaldehydes are inexpensive and highly pure and, therefore, prove useful as intermediates for drugs and pesticides and as perfumes and brighteners for plates.

We claim:

1. A method for the production of a substituted benzaldehyde represented by the general formula II:

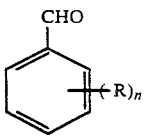

(II)

wherein R stands for methoxy group, tertiary butyl group, or phenoxy group and n for an integer of the value of 1 to 3, by the catalytic gas-phase oxidation of a substituted toluene represented by the general formula I:

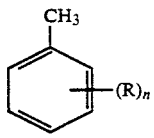

(I)

wherein R and n have the same meanings as defined above, with a molecular oxygen-containing gas in the presence of a catalyst composition represented by the general formula III:

 (III)

wherein V stands for vanadium, O for oxygen, X is as least one element selected from the group consisting of rubidium and cesium and Y is at least one element selected from the group consisting of copper, silver, phosphorus, antimony and bismuth, and the subscripts 1, b, c, and d jointly represent such an atomic ratio of the relevant elements that b has a value in the range of 0.1 to 5, c has a value in the range of 0 to 5, and d has a value determined by the valencies of the other elements and the value of said atomic ratio.

2. A method according to claim 1, wherein said catalyst composition is represented by the formula, $V_1\text{-(Rb and/or Cs)}_{0.2-1.0}\text{-(at least one element selected from the group consisting of Cu, Ag, P, Sb, and Bi)}_{0-1.0}\text{-O}_d$.

3. A method for the production of a substituted benzaldehyde represented by the general formula II:

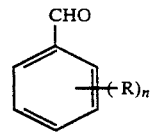

(II)

wherein R stands for methoxy group, tertiary butyl group, or phenoxy group, n for an integer of the value of 1 to 3, by the catalytic gas-phase oxidation of a substituted toluene represented by the general formula I:

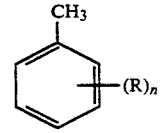

(I)

wherein R and n have the same meanings as defined above, with a molecular oxygen-containing gas in the presence of a catalyst composition represented by the general formula III:

 (III)

wherein V stands for vanadium, O for oxygen, wherein X is potassium and at least one element selected from the group consisting of rubidium and cesium and Y is at least one element selected from the group consisting of copper, silver, phosphorus, antimony and bismuth, and the subscripts 1, b, c, and d jointly represent such an atomic ratio of the relevant elements that b has a value in the range of 0.1 to 5, c has a value in the range of 0 to 5, and d has a value determined by the valencies of the other elements and the value of said atomic ratio.

4. A method according to claim 3, wherein said catalyst composition is represented by the formula, $V_1\text{-(Rb and/or Cs)}_{0.01-1.0}\text{-K}_{0.01-1.0}\text{-(at least one element selected from the group consisting of Cu, Ag, P, Sb, and Bi)}_{0-1.0}\text{-O}_d$.

5. A method for the production of a substituted benzaldehyde represented by the general formula II:

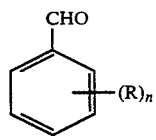

(II)

wherein R stands for methoxy group, tertiary butyl group, or phenoxy group and n for an integer of the value of 1 to 3, by the catalytic gas-phase oxidation of a substituted toluene represented by the general formula I:

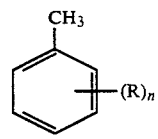

(I)

wherein R and n have the same meanings as defined above, with a molecular oxygen-containing gas in the presence of a catalyst composition represented by the general formula III:

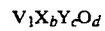 (III)

wherein V stands for vanadium, O for oxygen, X is thallium and at least one alkali metal selected from the group consisting of potassium, rubidium and cesium and Y is at least one element selected from the group consisting of copper, silver, phosphorus, antimony and bismuth, and the subscripts 1, b, c, and d jointly represent such an atomic ratio of the relevant elements that b has a value in the range of 0.1 to 5, c has a value in the range of 0 to 5, and d has a value determined by the valencies of the other elements and the value of said atomic ratio.

6. A method according to claim 5, wherein said catalyst composition is represented by the formula, $V_1\text{Tl}_{0.01-1.0}\text{-(at least one element selected from the group consisting of K, Rb, and Cs)}_{0-1.0}\text{-(at least one element selected from the group consisting of Cu, Ag, P, Sb, and Bi)}_{0-1.0}\text{-O}_d$.

* * * * *